United States Patent
Wu et al.

(10) Patent No.: US 7,613,511 B2
(45) Date of Patent: Nov. 3, 2009

(54) IMPLANTABLE VAGAL STIMULATOR FOR TREATING CARDIAC ISCHEMIA

(75) Inventors: Eugene Yu-Chun Wu, Shoreview, MN (US); Imad Libbus, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 11/075,838

(22) Filed: Mar. 9, 2005

(65) Prior Publication Data
US 2006/0206158 A1 Sep. 14, 2006

(51) Int. Cl.
*A61N 1/08* (2006.01)
*A61N 1/365* (2006.01)
*A61B 5/0472* (2006.01)

(52) U.S. Cl. .................. 607/9; 607/17; 607/118; 600/513

(58) Field of Classification Search .......... 607/2, 607/118, 9, 17, 44; 600/513
See application file for complete search history.

(56) References Cited

U.S. PATENT DOCUMENTS

| | | | | |
|---|---|---|---|---|
| 5,330,507 A | * | 7/1994 | Schwartz | 607/14 |
| 6,128,526 A | * | 10/2000 | Stadler et al. | 600/517 |
| 6,368,284 B1 | * | 4/2002 | Bardy | 600/508 |
| 6,904,318 B2 | * | 6/2005 | Hill et al. | 607/9 |
| 7,072,711 B2 | * | 7/2006 | Girouard et al. | 607/3 |
| 7,096,064 B2 | * | 8/2006 | Deno et al. | 607/9 |
| 2002/0107553 A1 | * | 8/2002 | Hill et al. | 607/18 |
| 2002/0165586 A1 | * | 11/2002 | Hill et al. | 607/9 |
| 2004/0172083 A1 | * | 9/2004 | Penner | 607/35 |
| 2005/0115561 A1 | * | 6/2005 | Stahmann et al. | 128/200.24 |
| 2005/0149143 A1 | * | 7/2005 | Libbus et al. | 607/44 |

OTHER PUBLICATIONS

"On-Line Medical Dictionary", http://cancerweb.ncl.ac.uk/omd/, (Archived Sep. 13, 2002), 1 Page.
Andersen, C, et al., "Does pain relief with spinal cord stimulation for angina conceal myocardial infarction?", *British Heart Journal*, 71(5), (May 1994), 419-21.
Bibevski, S., et al., "Ganglionic mechanisms contribute to diminished vagal control in heart failure", Circulation, 99(22), (Jun. 8, 1999), 2958-63.
Dickerson, L. W., "Parasympathetic neurons in the cranial medial ventricular fat pad on the dog heart selectively decrease ventricular contractility", *Journal of the Autonomic Nervous System*, 70(1-2), (May 28, 1998), 129-41.
George, M. S., et al., "Vagus nerve stimulation therapy: a research update", *Neurology*, 59(6 Suppl 4) (Sep. 24, 2002), S56-61.
George, M. S., "Vagus nerve stimulation: a new tool for brain research and therapy", *Biological Psychiatry*, 47(4), (Feb. 15, 2000), 287-95.

(Continued)

*Primary Examiner*—Carl H Layno
*Assistant Examiner*—Natasha N Patel
(74) *Attorney, Agent, or Firm*—Schwegman, Lundberg & Woessner, P.A.

(57) ABSTRACT

A device and method for treating cardiac ischemia with vagal stimulation is disclosed. In one embodiment, an implantable device is configured to deliver vagal stimulation upon obtaining an indication of cardiac ischemia by analysis of a recorded electrogram.

16 Claims, 4 Drawing Sheets

OTHER PUBLICATIONS

Kim, M. C., et al., "Refractory angina pectoris: mechanism and therapeutic options", *Journal of the American College of Cardiology*, 39(6), (Mar. 20, 2002), 923-34.

Lathrop, D. A., "On the neural connection", *Journal of Cardiovascular Electrophysiology*, vol. 12, No. 7, (Jul. 2001), 841-844.

Tsuboi, M., "Inotropic, chronotropic, and dromotropic effects mediated via parasympathetic ganglia in the dog heart", *American Journal of Physiology—Heart & Circulatory Physiology*, vol. 279, No. 3, (Sep. 2000), H1201-7.

Zamotrinsky, A. V., et al., "Vagal neurostimulation in patients with coronary artery disease", *Autonomic Neuroscience-Basic & Clinical*, 88(1-2), (Apr. 12, 2001), 109-116.

\* cited by examiner

ST SEGMENT

IMPLANTABLE VAGAL STIMULATOR FOR TREATING CARDIAC ISCHEMIA

FIELD OF THE INVENTION

This invention pertains to methods and devices for treating cardiac disease.

BACKGROUND

Coronary artery disease (CAD) occurs when the coronary arteries that supply blood to the heart muscle become hardened and narrowed due to atherosclerosis. The arteries harden and become narrow due to the buildup of plaque on the inner walls or lining of the arteries. Blood flow to the heart is reduced as plaque narrows the coronary arteries. This decreases the oxygen supply to the heart muscle. CAD is the most common type of heart disease which is the leading cause of death in the U.S. in both men and women.

When blood flow and oxygen supply to the heart are reduced or cut off, patients often experience chest pain or discomfort, referred to as angina pectoris. Angina pectoris serves as a useful warning of insufficient myocardial perfusion which can lead to a more serious situation such as a heart attack or cardiac arrhythmia. A heart attack or myocardial infarction happens when a blood clot in an atherosclerotic suddenly cuts off most or all blood supply to part of the heart. Cells in the heart muscle that do not receive enough oxygen-carrying blood begin to die which can cause permanent damage to the heart muscle. Cardiac arrhythmias are changes in the normal rhythm of the heartbeats, some of which can be lethal.

Patients who experience anginal episodes are commonly treated either with medication or by surgical revascularization. Certain patients, however, are not responsive to medical therapy nor are they appropriately treated with surgery. The present disclosure relates to an alternative mode of therapy for treating CAD patients who experience angina pectoris.

SUMMARY

A device and method for treating cardiac ischemia with vagal stimulation is disclosed. In one embodiment, an implantable device is configured to deliver vagal stimulation upon obtaining an indication of cardiac ischemia by analysis of a recorded electrogram.

DETAILED DESCRIPTION

The present disclosure relates to an implantable device for delivering vagal stimulation therapy in response to an indication that an episode of cardiac ischemia is occurring. The vagus nerve provides parasympathetic stimulation to the heart which counteracts the effects of increased sympathetic activity in a manner which is beneficial when the blood supply to the heart is compromised. Stimulation of the vagus nerve at either a pre-ganglionic or post-ganglionic site produces dilation of the coronary arteries and a reduced workload on the heart. In one embodiment, the indication of cardiac ischemia is chest pain, and the device is operated by the patient to provide relief from angina pectoris. Since vagal stimulation acts on the physiological cause of the angina rather than masking the symptoms, chest pain due to more serious conditions such as a heart attack will not be affected. Vagal stimulation can therefore relieve the pain of angina pectoris and may also reduce the probability of a heart attack or arrhythmia occurring. Other embodiments may use the sensing modalities of the implantable device for providing an indication of cardiac ischemia with the device then configured to automatically deliver vagal stimulation therapy in response thereto.

Figure 1:
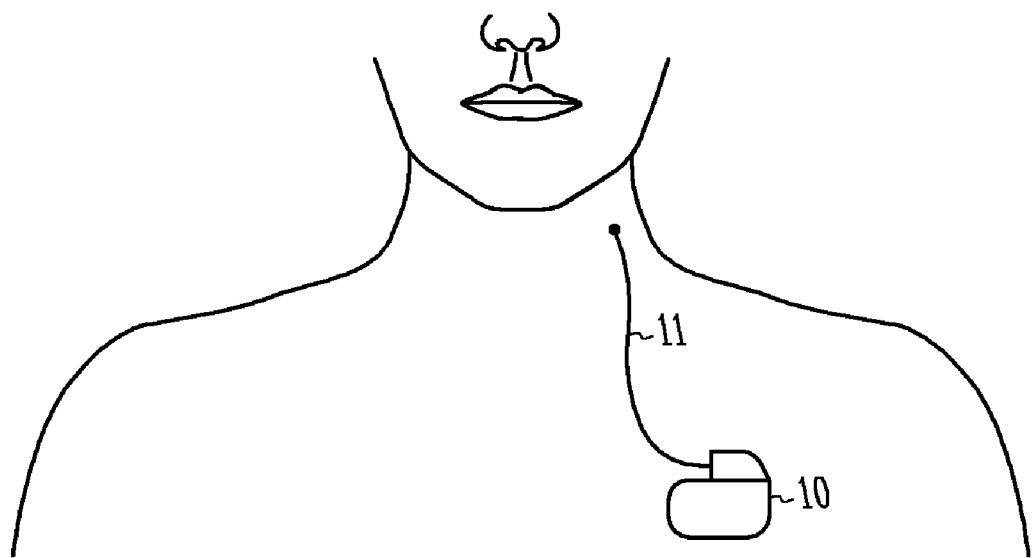
FIG. 1 is a physical depiction of an implantable device for delivering vagal stimulation.
Figure 1:
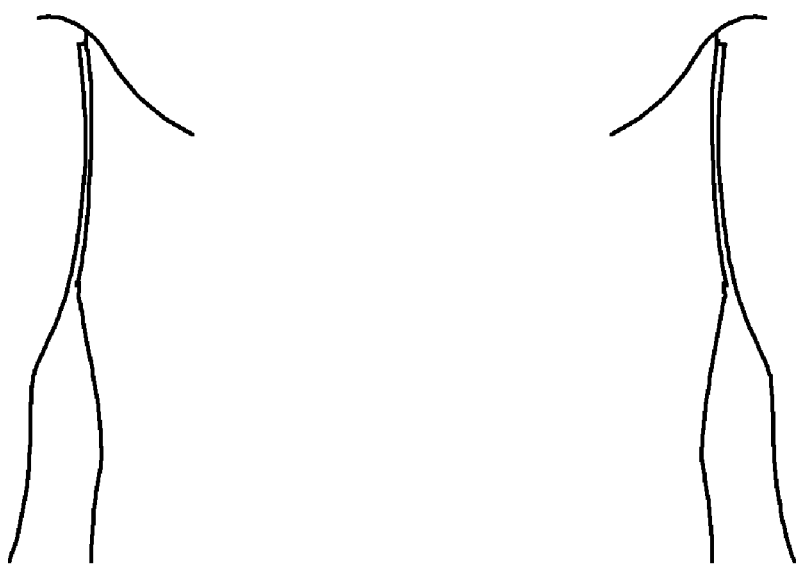

FIG. 1 shows an implantable vagal stimulator which includes a housing 10 implanted subcutaneously on a patient's chest. Electrical pulse generation circuitry within the housing 10 is connected to a lead 11 which incorporates a bipolar or unipolar electrode at its distal end for stimulating nervous tissue. In one embodiment, the lead 11 is tunneled subcutaneously to a specific pre-ganglionic or post-ganglionic stimulation site near the vagus nerve. Other techniques for disposing an electrode for vagal stimulation could also be used such as a lead which is intravascularly disposed near an appropriate stimulation site. In some patients, for example, a preferred intravascular location would be in the internal jugular vein. Other types of leads and/or electrodes may also be employed such as a nerve cuff electrode which is placed, for example, around the cervical vagus nerve bundle to provide vagal stimulation. By means of a magnetically or tactilely actuated switch, the patient is able to cause the stimulator to deliver stimulation pulses to the vagus nerve when the patient experiences angina. As described below, the device may also incorporate additional circuitry for detecting cardiac ischemia and for automatically delivering vagal stimulation.

Figure 2:
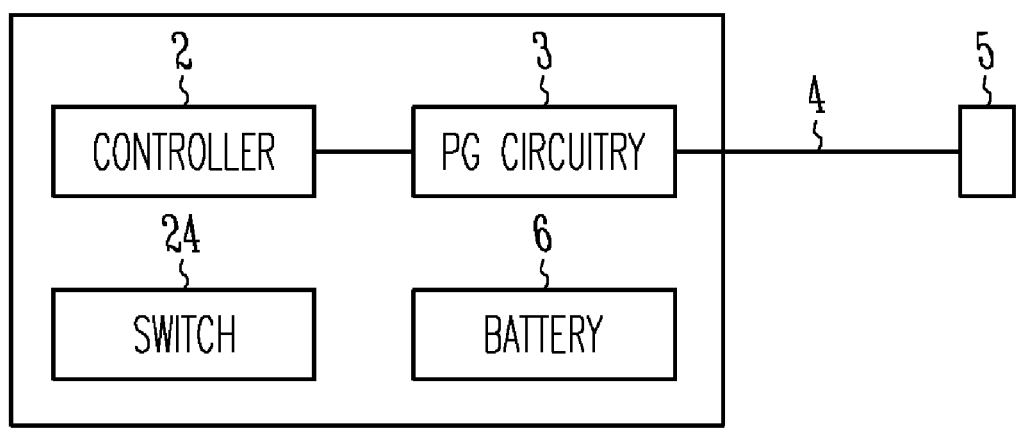
FIG. 2 is a block diagram of an implantable device for delivering vagal stimulation.

FIG. 2 is a system diagram of the electronic components of the vagal stimulator contained within the housing 10. A programmable electronic controller 2 is interfaced to pulse generation circuitry 3 and controls the output of vagal stimulation pulses. The controller 2 may be made up of a microprocessor communicating with a memory, where the memory may comprise a ROM (read-only memory) for program storage and a RAM (random-access memory) for data storage. The controller could also be implemented by other types of logic circuitry (e.g., discrete components or programmable logic arrays) using a state machine type of design. The pulse generation circuitry may be similar to that used in cardiac pacemakers and provides electrical stimulation pulses to a vagal stimulation electrode 5 via the lead 4. A battery 6 also contained within the housing provides power to the device.

A magnetically or tactilely actuated switch 24 interfaced to the controller 2 allows the patient to initiate the delivery of the vagal stimulation pulses upon the onset of anginal symptoms. Once begun, the vagal stimulation pulses may continue to be delivered for a predetermined length of time or according to a predetermined schedule. The frequency and amplitude of the vagal stimulation pulses in this embodiment are programmable parameters, the optimal values of which depend upon the stimulation site and type of stimulation electrode.

Figure 3:
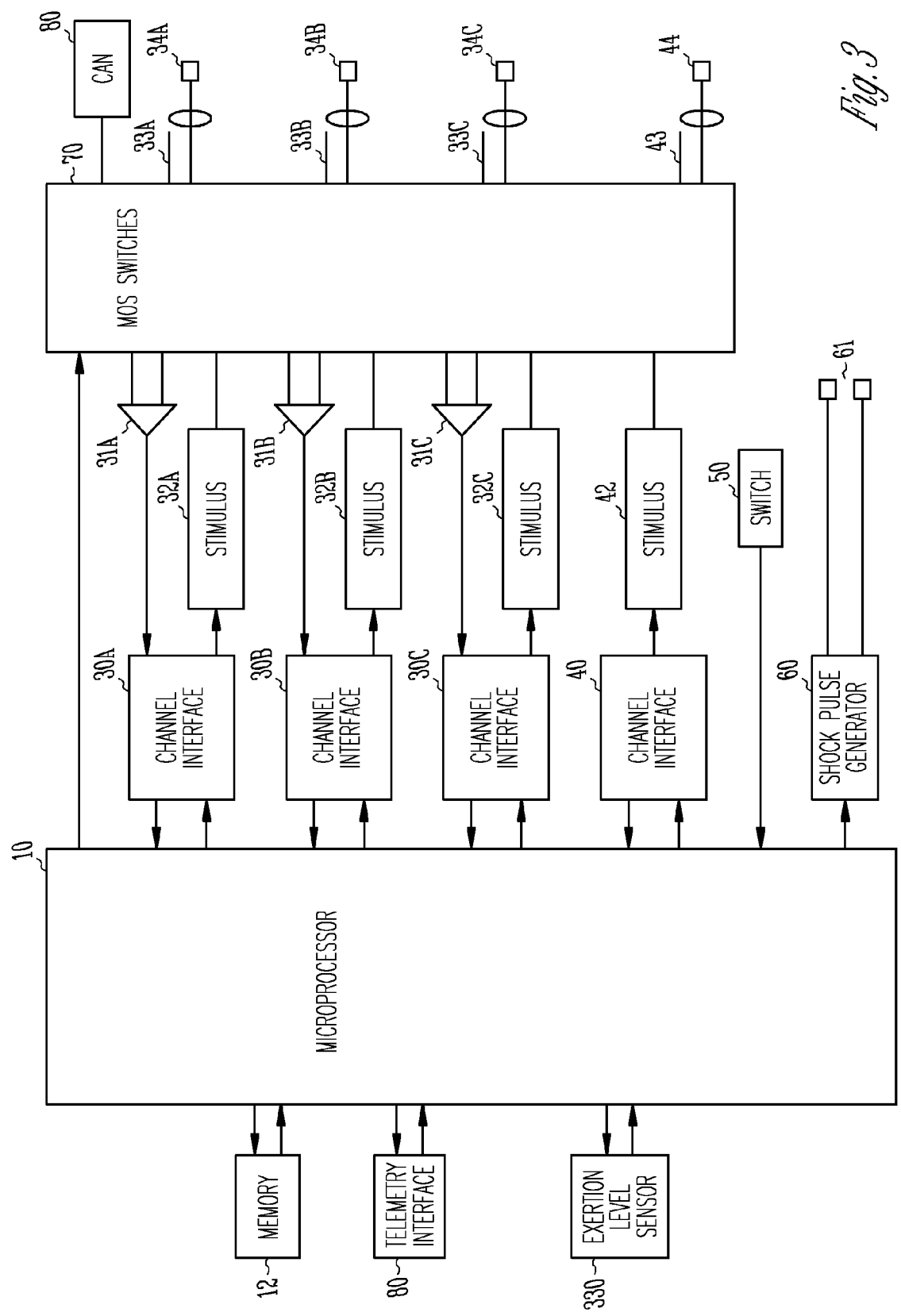
FIG. 3 is a block diagram of an implantable cardiac device with the capability of delivering vagal stimulation.

In another embodiment, the vagal stimulator is incorporated into an implantable cardiac rhythm management device which has cardiac pacing and/or cardioversion/defibrillation functionality. FIG. 3 shows a system diagram of an exemplary microprocessor-based cardiac device. The device is battery-powered and equipped with multiple sensing and pacing channels which may be physically configured to sense and/or pace the atria or the ventricles in a variety of pacing modes including conventional bradycardia pacing and cardiac resynchronization pacing. The controller 10 of the device is a microprocessor which communicates with a memory 12 via a bidirectional data bus. Shown in FIG. 3 are three exemplary sensing and pacing channels designated "a" through "c" comprising bipolar leads with ring electrodes 34a-c and tip electrodes 33a-c, sensing amplifiers 31a-c, pulse generators 32a-c, and channel interfaces 30a-c. Each channel thus includes a pacing channel made up of the pulse generator connected to the electrode and a sensing channel made up of the sense amplifier connected to the electrode. The channel interfaces 30a-c communicate bidirectionally with microprocessor 10, and each interface may include analog-to-digital converters for digitizing sensing signal inputs from the sensing amplifiers and registers that can be written to by the microprocessor in order to output pacing pulses, change the pacing pulse amplitude, and adjust the gain and threshold values for the sensing amplifiers. The sensing circuitry of the pacemaker detects a chamber sense, either an atrial sense or ventricular sense, when an electrogram signal (i.e., a voltage sensed by an electrode representing cardiac electrical activity) generated by a particular channel exceeds a specified detection threshold. Pacing algorithms used in particular pacing modes employ such senses to trigger or inhibit pacing, and the intrinsic atrial and/or ventricular rates can be detected by measuring the time intervals between atrial and ventricular senses, respectively. The electrodes of each bipolar lead are connected via conductors within the lead to a MOS switching network 70 controlled by the microprocessor. The switching network is used to switch the electrodes to the input of a sense amplifier in order to detect intrinsic cardiac activity and to the output of a pulse generator in order to deliver a pacing pulse. The switching network also enables the device to sense or pace either in a bipolar mode using both the ring and tip electrodes of a lead or in a unipolar mode using only one of the electrodes of the lead with the device housing or can 80 serving as a ground electrode. A shock pulse generator 60 is also interfaced to the controller for delivering a defibrillation shock via a pair of shock electrodes 61 to the atria or ventricles upon detection of a shockable tachyarrhythmia. A minute ventilation sensor 330 or other sensor that measures a parameter related to metabolic demand enables the controller to adapt the pacing rate in accordance with changes in the patient's physical activity. A telemetry interface 80 is also provided which enables the controller to communicate with an external programmer or remote monitor. A neural stimulation channel is incorporated into the device for delivering vagal stimulation which includes a bipolar lead with a ring electrode 44 and a tip electrode 43, a pulse generator 42, and a channel interface 40.

A magnetically or tactilely actuated switch 50 for initiating (or stopping) delivery of vagal stimulation may be incorporated into the implantable cardiac device such as shown in FIG. 3. The switch 50 may be operated by the patient upon onset of anginal symptoms similar to the operation of the embodiment illustrated in FIG. 2. Either instead of, or in addition to, a magnetically or tactilely actuated switch, vagal stimulation may be triggered automatically upon the sensing of a particular condition by the implantable device utilizing its available sensing modalities. Once automatic delivery of vagal stimulation is begun, the device may be configured so that the patient may stop the stimulation by actuating switch 50.

One condition which may be used to trigger automatic delivery of vagal stimulation is cardiac ischemia. Cardiac ischemia may be detected from a morphology analysis of an electrogram from an intrinsic or a paced beat, the latter sometimes referred to as an evoked response. The electrogram for detection of ischemia is recorded from a sensing channel that senses the depolarization and repolarization of the myocardium during a cardiac cycle. The sensing channel used for this purpose may be a sensing channel used for detecting cardiac arrhythmias and/or intrinsic beats or may be a dedicated channel. In order to detect ischemic changes in an electrogram, it may be preferable to record the electrogram with a unipolar electrode that "sees" a larger volume of the myocardium as a wave of electrical activity spreads than a bipolar electrode. In order to detect an ischemic change, the electrogram can be compared with a reference electrogram to see if an increased current of injury is present. The comparison may involve, for example, cross-correlating the recorded and reference electrograms or comparing ST segment amplitudes, slopes, or integrations with reference values.

In order to detect whether the patient is experiencing cardiac ischemia during pacing, the controller is programmed to analyze the recorded electrogram of an evoked response and look for a "current of injury." When the blood supply to a region of the myocardium is compromised, the supply of oxygen and other nutrients can become inadequate for enabling the metabolic processes of the cardiac muscle cells to maintain their normal polarized state. An ischemic region of the heart therefore becomes abnormally depolarized during at least part of the cardiac cycle and causes a current to flow between the ischemic region and the normally polarized regions of the heart, referred to as a current of injury. A current of injury may be produced by an infarcted region that becomes permanently depolarized or by an ischemic region that remains abnormally depolarized during all or part of the cardiac cycle. A current of injury results in an abnormal change in the electrical potentials measured by either a surface electrocardiogram or an intracardiac electrogram. If the abnormal depolarization in the ventricles lasts for the entire cardiac cycle, a zero potential is measured only when the rest of the ventricular myocardium has depolarized, which corresponds to the time between the end of the QRS complex and the T wave in an electrogram and is referred to as the ST segment. After repolarization of the ventricles, marked by the T wave in an electrogram, the measured potential is influenced by the current of injury and becomes shifted, either positively or negatively depending upon the location of the ischemic or infarcted region, relative to the ST segment. Traditionally, however, it is the ST segment that is regarded as shifted when an abnormal current of injury is detected by an electrogram or electrocardiogram. A current injury produced by an ischemic region that does not last for the entire cardiac cycle may only shift part of the ST segment, resulting in an abnormal slope of the segment. A current of injury may also be produced when ischemia causes a prolonged depolarization in a ventricular region which results in an abnormal T wave as the direction of the wave of repolarization is altered.

Figure 4A:
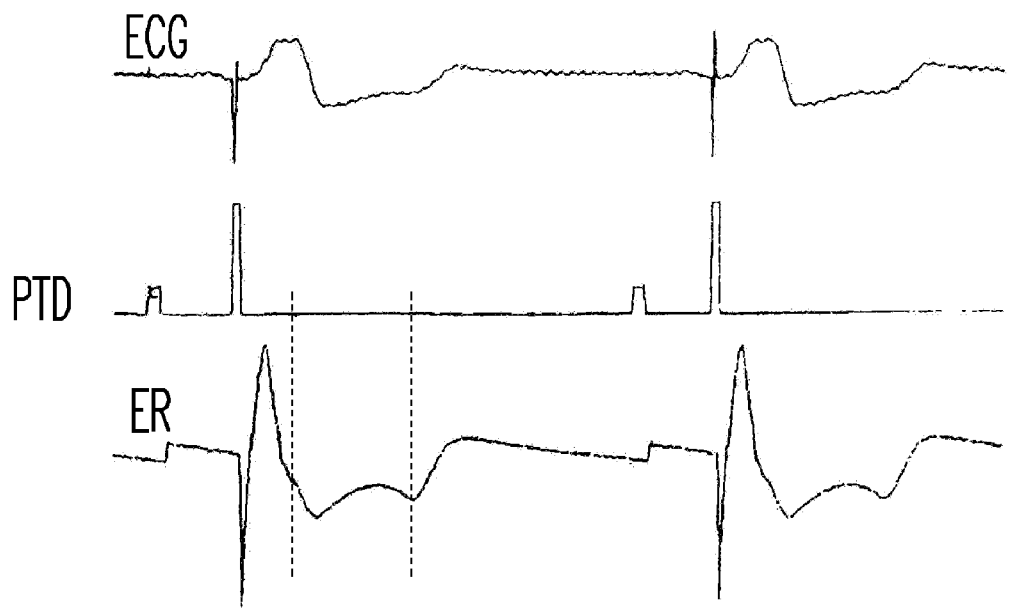
FIG. 4 illustrates ischemic changes in a recorded electrogram.
Figure 4B:
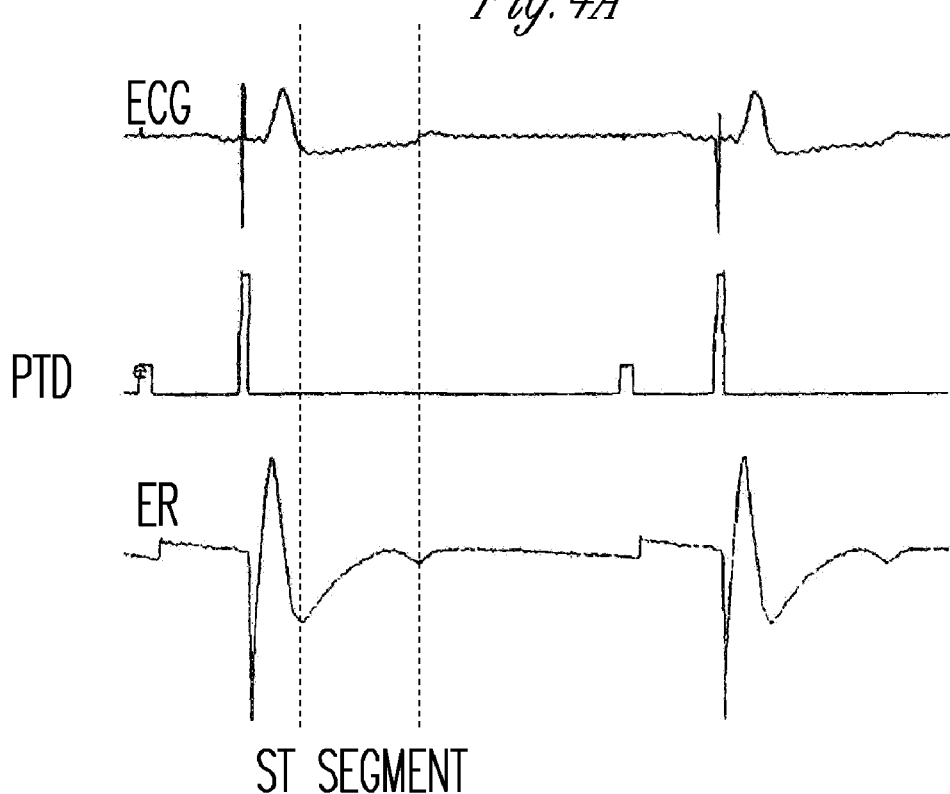

In order to detect a change in an electrogram indicative of ischemia, a recorded electrogram is analyzed and compared with a reference electrogram, which may either be a complete recorded electrogram or particular reference values representative of an electrogram. Because certain patients may always exhibit a current of injury in an electrogram (e.g., due to CAD or as a result of electrode implantation), the controller is programmed to detect ischemia by looking for an increased current of injury in the recorded electrogram as compared with the reference electrogram, where the latter may or may not exhibit a current of injury. FIG. 4 shows examples of evoked response data for two cases labeled A and B, where A is the baseline reference and B is during an acute ischemic episode. A surface electrocardiogram labeled ECG, a pacing timing diagram labeled PTD, and an electrogram labeled ER are illustrated for each case. The ST segment of the electrogram for case B is seen to have different amplitudes and slopes as compared with the amplitudes and slopes of the ST segment of the electrogram for case A. One way to look for an increased current of injury in the recorded electrogram is to compare the ST segment amplitude and/or slope with the amplitude and slope of a reference electrogram. Various digital signal processing techniques may be employed for the analysis, such as using first and second derivatives to identify the start and end of an ST segment. Other ways of looking for a current injury may involve, for example, cross-correlating the recorded and reference electrograms to ascertain their degree of similarity. The electrogram could be implicitly recorded in that case by passing the electrogram signal through a matched filter that cross-correlates the signal with a reference electrogram. The ST segment could also be integrated, with the result of the integration compared with a reference value to determine if an increased current of injury is present.

If a change in a recorded electrogram indicative of ischemia is detected, the controller may be programmed to deliver vagal stimulation therapy. Detection of cardiac ischemia may also be logged as a clinically significant event in the pacemaker's memory, where the event log and/or the recorded electrogram exhibiting the ischemia may then be later downloaded to a clinician for analysis via an external programmer.

Information derived from other analyses or other sensing modalities may also be used to more specifically detect cardiac ischemia. For example, dyspnea or other abnormal breathing patterns may be detected using a minute ventilation sensor by programming the controller to compare the transthoracic impedance signal from the sensor with a template representing the abnormal pattern. An indication of cardiac ischemia may then require an electrogram change indicative of ischemia and a dyspneic or other abnormal breathing pattern.

In one embodiment, vagal stimulation is delivered either upon manual operation by the patient of a tactilely or magnetically operated switch or upon detection of cardiac ischemia by the device from its sensing modalities (i.e., by morphology analysis of electrograms). In another embodiment, vagal stimulation is delivered only if the tactilely or magnetically actuated switch is operated by the patient and, in addition, the device detects ischemia by morphology analysis of an electrogram signal.

Automatic delivery of vagal stimulation may be delivered by an implantable device with appropriate sensing capabilities but with no capability for delivering cardiac pacing or cardioversion/defibrillation therapy. It may be desirable, however, to treat patients with such combination pacemaker/ICD devices configured to also deliver vagal stimulation. Patients with CAD are prone to the development of arrhythmias which can then be treated with shock therapy. Also, vagal stimulation produces bradycardia which in some patients may lead to syncope. Bradycardia may also result in lessened cardiac perfusion which exacerbates the cardiac ischemia. These problems can be dealt with by configuring the device to deliver atrial and/or ventricular pacing in a bradycardia pacing mode which enforces a minimum heart rate with timed escape intervals. Resynchronization pacing (e.g., biventricular or left ventricle-only pacing) may also be useful in bradycardic situations in order to ensure hemodynamically efficient contractions.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A method for treating cardiac ischemia, comprising:
   configuring an implantable device to monitor for an indication that an episode of cardiac ischemia is occurring, wherein such indication of cardiac ischemia includes changes in cardiac electrical activity;
   configuring the implantable device with a magnetically or tactilely actuated switch;
   configuring the implantable device to deliver electrical stimulation to the vagus nerve upon obtaining an indication of cardiac ischemia and upon actuation of the magnetically or tactilely actuated switch;
   configuring the implantable device to inhibit delivery of electrical stimulation to the vagus nerve unless both an indication of cardiac ischemia is obtained and the magnetically or tactilely actuated switch is actuated;
   configuring the implantable device to cease delivery of the electrical stimulation to the vagus nerve after a predetermined length of time; and,
   configuring the implantable device to cease delivery of the electrical stimulation to the vagus nerve upon actuation of the magnetically or tactilely actuated switch.

2. The method of claim 1 further comprising configuring the implantable device to deliver electrical stimulation to the vagus nerve in conjunction with the delivery of pacing pulses in a bradycardia pacing mode that enforces a minimum heart rate, wherein the pacing pulses are delivered as biventricular or left ventricle-only pacing.

3. The method of claim 1 further comprising obtaining an indication of cardiac ischemia by analyzing the morphology of a recorded electrogram.

4. The method of claim 3 further comprising configuring the implantable device to detect a dyspneic breathing pattern by measuring transthoracic impedance and wherein the indication of cardiac ischemia further includes detection of a dyspneic breathing pattern.

5. The method of claim 1 further comprising configuring the implantable device for:
   delivering paces to a cardiac chamber in accordance with a programmed pacing mode;
   sensing an evoked response to a pace and recording an electrogram therefrom; and,
   analyzing the recorded electrogram in order to detect a change indicative of cardiac ischemia.

6. The method of claim 5 wherein a change in the recorded electrogram indicative of cardiac ischemia are detected by looking for an increased current of injury in the recorded electrogram.

7. The method of claim 6 wherein an increased current of injury is looked for by cross-correlating the recorded electrogram with a reference electrogram.

8. The method of claim 1 further comprising configuring the implantable device to deliver vagal stimulation upon manual operation of the tactilely or magnetically actuated switch of the implantable device.

9. An implantable cardiac device, comprising:
   one or more sensing channels for sensing cardiac activity;
   a neural stimulation channel for delivering vagal stimulation;
   a controller programmed to record an electrogram from the sensing channel and analyze the recorded electrogram;

wherein the controller is programmed to obtain an indication of cardiac ischemia if a change indicative of cardiac ischemia is detected in the recorded electrogram;

a magnetically or tactilely actuated switch;

wherein the controller is programmed to delivery vagal stimulation upon obtaining an indication of cardiac ischemia and actuation of the magnetically or tactilely actuated switch;

wherein the controller is programmed to inhibit delivery of electrical stimulation to the vagus nerve unless both an indication of cardiac ischemia is obtained and the magnetically or tactilely actuated switch is actuated;

wherein the controller is programmed to cease delivery of the vagal stimulation after a predetermined length of time; and, wherein the controller is programmed to cease delivery of the vagal stimulation upon actuation of the magnetically or tactilely actuated switch.

10. The device of claim 9 further comprising:

a pacing channel for pacing a cardiac chamber;

wherein the controller is programmed to deliver paces to the cardiac chamber in accordance with a programmed pacing mode; and, wherein the controller is programmed to record an electrogram from the sensed evoked response and analyze the recorded electrogram in order to detect a change indicative of cardiac ischemia.

11. The device of claim 9 wherein the controller is further programmed to log a detected change in the electrogram indicative of cardiac ischemia as a clinically significant event.

12. The device of claim 9 further comprising:

a transthoracic impedance sensor for detecting a patient's breathing pattern; and, wherein the controller is programmed to obtain an indication of cardiac ischemia only if a change indicative of cardiac ischemia is detected in the recorded electrogram and a dyspneic breathing pattern is detected.

13. The device of claim 9 wherein the controller is further programmed to deliver vagal stimulation upon actuation of the magnetically or tactilely actuated switch.

14. The device of claim 9 further comprising pacing channels for delivering biventricular or left ventricle-only pacing and wherein the controller is further programmed to deliver vagal stimulation in conjunction with the delivery of pacing pulses in a bradycardia pacing mode that enforces a minimum heart rate, wherein the pacing pulses are delivered as biventricular or left ventricle-only pacing.

15. The device of claim 9 wherein the controller is programmed to detect a change in the recorded electrogram indicative of cardiac ischemia by looking for an increased current of injury in the recorded electrogram.

16. The device of claim 15 wherein the controller is programmed to look for an increased current of injury for by cross-correlating the recorded electrogram with a reference electrogram.

* * * * *